United States Patent [19]

Rigterink et al.

[11] Patent Number: 4,518,804

[45] Date of Patent: May 21, 1985

[54] HALO(ALKOXY/ALKYLTHIO)-BENZENAMINES

[75] Inventors: Raymond H. Rigterink, Midland, Mich.; Barat Bisabri-Ershadi, Pittsburg, Calif.

[73] Assignee: The Dow Chemical Company, Midland, Mich.

[21] Appl. No.: 520,032

[22] Filed: Aug. 3, 1983

Related U.S. Application Data

[62] Division of Ser. No. 401,492, Jul. 26, 1982.

[51] Int. Cl.³ .................. C07C 87/60; C07C 149/42
[52] U.S. Cl. .................. 564/442; 564/440; 564/28; 564/29; 564/49; 564/52; 564/53; 564/54; 260/453 AR; 260/454
[58] Field of Search .................. 564/442, 440

[56] References Cited

U.S. PATENT DOCUMENTS

| 2,745,874 | 5/1956 | Schetty | 564/54 |
| 3,868,399 | 2/1975 | Karabinos | 564/442 |
| 4,404,402 | 9/1983 | Ladner | 564/305 |

Primary Examiner—Charles F. Warren
Assistant Examiner—Harry B. Shubin

[57] ABSTRACT

Novel N-aroyl N'-phenyl urea compounds having halogen substituents in the 2- and 5-position of the phenyl radical possess exceptional insecticidal activity.

3 Claims, No Drawings

HALO(ALKOXY/ALKYLTHIO)-BENZENAMINES

CROSS-REFERENCE TO RELATED APPLICATION

This is a division of application Ser. No. 401,492 filed July 26, 1982.

BACKGROUND OF THE INVENTION

This invention relates to novel N-benzoyl-N'-haloalkoxyphenyl ureas, processes for producing them, insecticidal compositions containing them and a method for controlling certain insects.

A large number of insecticidal derivatives of urea are known in the art, such as, for example, U.S. Pat. Nos. 4,173,638; 4,005,223; 4,170,657; 4,139,636; 4,089,975; 3,748,356; 3,933,908; 4,013,717; 4,276,310 and 4,277,499 and German Pat. No. 2,848,794.

The N-benzoyl-N'-haloalkoxyphenyl ureas of this invention have greater activity and a broader spectrum of activity than the related compounds of the prior art.

SUMMARY OF THE INVENTION

The novel compounds of this invention are N-benzoyl-N'-haloalkoxyphenyl ureas having the formula:

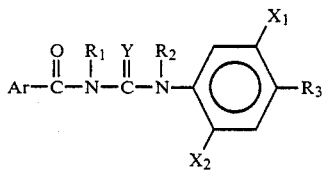

wherein Ar is a substituted phenyl, pyridyl, or pyrimidinyl radical wherein the substituents are chloro, bromo, fluoro, $C_1$–$C_3$ alkoxy, with the proviso that at least one substitutent is positioned ortho to the carbonyl group; $R_1$ and $R_2$ are individually H or $C_1$–$C_4$ alkyl or together they form the group

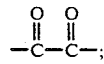

Y is O or S; $X_1$ and $X_2$ are independently halogen, and $R_3$ is a $C_1$–$C_4$ haloalkyl, haloalkoxy or haloalkylthio group.

The invention also provides insecticidal compositions comprising an insecticidally effective amount of the above-described N-benzoyl-N'-haloalkoxyphenyl ureas in admixture with a suitable carrier or adjuvant therefore, and a method for killing and/or controlling insects which comprises applying the active compound, alone or in admixture with a carrier, to the insects, the insective larvae or their habitats.

DETAILED DESCRIPTION OF THE INVENTION

The preferred compounds of this invention are those having the formula

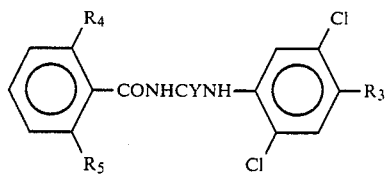

wherein $R_4$ is F or Cl; $R_5$ is F, Cl or H; Y is O or S and $R_3$ is $OCF_2CHF_2$, $OCF_2CHFCl$, $OCF_2CHFBr$ or $OCF_3$. Most preferably Y is oxygen, $R_3$ is $OCF_2CHClF$, $OCF_2CHF_2$ or $OCF_2CHFBr$, $R_4$ and $R_5$ are both F, one of $R_4$ and $R_5$ is F and the other Cl, or $R_4$ is Cl and $R_5$ is H.

These novel compounds can be prepared by methods analogous to those known in the art, with the appropriate choice of starting materials and as illustrated in the following examples.

EXAMPLE 1

(A) Preparation of 2,5-dichloro-4-(1,1,2,2-tetrafluoroethoxy)benzenamine

A mixture of 100 ml dimethylformamide (DMF), 75 g (0.035 mole) 4-amino-2,5-dichlorophenol, hydrochloride, and 3.0 g (0.05 mole) KOH (pellets ground to powder) was placed in a 500 ml 3-necked round bottom flask fitted with a mechanical stirrer, thermometer and reflux condenser and was stirred for about 1 hour. It was then heated to 85° C. with stirring and 6.0 g (0.06 mole) of tetrafluoroethylene was bubbled in while heating at 85°–90° C. The addition took about 10 minutes. The reactor and contents were cooled in an ice water bath and 200 ml of water were added. The product was extracted with 200 ml methylene chloride and then again with 100 ml methylene chloride. The extracts were combined and the solvents removed by vacuum distillation. A residue (7 g) remained.

(B) Preparation of N-(((2,5-dichloro-4-(1,1,2,2-tetrafluoroethoxy)phenyl)amino)carbonyl)-2,6-difluorobenzamide A mixture of 100 ml toluene (distilled in glass), 7 g (0.025 mole) crude 2,5-dichloro-4-(1,1,2,2-tetrafluoroethoxy)benzenamine (prepared as above) and 5 g (0.025 mole) of 2,6-difluorobenzoyl isocyanate was placed in a 500 ml 3-necked round bottom flask fitted with a mechanical stirrer, thermometer and reflux condenser and was heated under reflux for 1 hour while stirring. The clear solution was cooled with an ice water bath and let stand at room temperature overnight. The solid precipitate (A) was removed by suction filtration, washed with a little toluene and dried at room temperature. The toluene was removed from the filtrate in a rotary evaporator leaving a residue of 7 g of a dark red oily solid. This was treated with 30 ml acetic acid and 5 ml water and heated to give a clear solution. After cooling in an ice bath, the solid precipitate (B) was removed by suction filtration and washed with cold aqueous acetic acid. The filter cake was dried at room temperature. Weight of (A) was 2.8 g, white solid, m.p. 172°–175° C. NMR indicated that it was the desired product. Weight of (B) was 2.4 g, m.p. 170°–172° C. The samples were combined and dissolved in 50 ml acetic acid and 5 ml water, heated to 100° C., cooled in an ice water bath and the precipitate filtered off. The filter cake was washed with a little cold aqueous acetic acid and dried at room temperature. Weight 5.0 g, white solid, m.p. 174°-176° C. NMR analysis indicated it was the desired product.

Analysis: Calculated: C, 41.67; H, 1.75; N, 6.08. Found: C, 41.6; H, 1.89; N, 6.10.

EXAMPLE 2

(A) Preparation of 4-(2-chloro-1,1,2-trifluoroethoxy)-2,5-dichlorobenzenamine

A solution of 25 g (0.12 mole) of 4-amino-2,5-dichlorophenol hydrochloride in 200 ml dimethylformamide was placed in a 500 ml 3-necked round bottom flask, fitted with a mechanical stirrer, thermometer, reflux condenser and sparger, and 13.4 g (0.24 mole) of potassium hydroxide pellets ground to powder were added. The mixture was heated to 90° C. with stirring under a nitrogen blanket. Then 21 g (0.18 mole) chlorotrifluoroethylene was bubbled in, while stirring and heating at 90° to 100° C., in about ½ hour. Stirring was continued for 5 minutes, the mixture cooled in an ice water bath, 500 ml of water were added and the resulting mixture extracted with 250 ml methylene dichloride and then 100 ml methylene dichloride. The extracts were combined, washed with 250 ml water and the methylene dichloride removed in a rotary evaporator. The residue was distilled through a 1"×10" Vigreaux. The cut from 110° to 120° C. at 2 mm pressure was a light tan liquid. Weight 21 grams. Yield was 59 percent. NMR analysis verified structure.

(B) Preparation of N-(((2,5-dichloro-4-(2-chloro-1,1,2-trifluoroethoxy)-phenyl)amino)carbonyl)2,6-difluorobenzamide A solution of 5.9 g (0.02 mole) of the above prepared 4-(2-chloro-1,1,2-trifluoroethoxy)-2,5-dichlorobenzeneamine in 100 ml toluene was placed in a 500 ml 3-necked round bottom flask fitted with a mechanical stirrer, thermometer and reflux condenser and 5.5 g (0.03 mole) of 2,6-difluorobenzoyl isocyanate was added while stirring. The temperature rose from 23° to 34° C. in a few minutes. The mixture was heated under reflux while stirring for one hour giving a clear solution which was cooled in an ice water bath. The toluene was removed by evaporation in a rotary evaporator and 25 ml acetic acid and 5 ml water were added to the residue. The resulting mixture was heated to boiling, giving a clear solution, cooled in an ice water bath and suction filtered. The filter cake obtained was washed with a little cold aqueous acetic acid and dried at room temperature. Weight, 8.5 g of white solid. m.p. 177°-179° C. The structure was verified by NMR.

Analysis: Calculated: C, 40.23; H, 1.69; N, 5.87. Found: C, 40.8; H, 1.72; N, 5.94.

The percent yield was 89. This material was recrystallized from acetonitrile and dried giving a white solid melting at 181°-183° C.

EXAMPLE 3

Preparation of N-(((2,5-dichloro-4-(2-chloro-1,1,2-trifluoroethoxy)-phenyl)amino)carbonyl)2,6-dichlorobenzamide The procedure of Example 2(B) was repeated using 6.5 g (0.03 mole) of 2,6-dichlorobenzoyl isocyanate. After removing the toluene, the residue was dissolved in 100 ml 90 percent hot acetic acid. After cooling, filtering and drying, 7.0 g of white solid, melting at 198°-200° C. was obtained.

Analysis: Calculated: C, 37.64; H, 1.58; N, 5.49. Found: C, 38.44; H, 1.70; N, 5.60.

The product was recrystallized from acetonitrile and dried at room temperature. Weight 4.8 g. White needles. m.p. 204°-206° C.

Analysis: Found: C, 38.1; H, 1.6; H, 5.56.

EXAMPLE 4

Preparation of N-(((2,5-dichloro-4-(2-chloro-1,1,2-trifluoroethoxy)-phenyl)amino)carbonyl)-2-chlorobenzamide The procedure of Example 2(B) was repeated except to use 5.5 g (0.03 mole) of 2-chlorobenzoyl isocyanate. Obtained 6.5 g of white solid melting at 158°-160° C.

Analysis: Calculated: C, 40.36; H, 1.91; N, 5.89. Found: C, 40.9; H, 2.0; N, 5.86.

Employing the above procedures, the following compounds were prepared from the appropriate starting materials:

N-(((2,5-Dichloro-4-(2-bromo-1,1,2-trifluoroethoxy)-phenyl)amino)carbonyl)-2,6-difluorobenzamide.

M.P. 173°-176° C.

Analysis: Calcd: C, 36.81; H, 1.54; N, 5.37. Found: C, 37.56; H, 16.2; N, 5.43.

N-(((2,5-Dichloro-4-(2,2-dichloro-1,1-difluoroethoxy)phenyl)amino)carbonyl)-2,6-difluorobenzamide.

M.P. 180°-182° C.

Analysis: Calcd: C, 38.89; H, 1.63; N, 5.67. Found: C, 40.0; H, 1.75; N, 5.86.

N-(((2,5-Dichloro-4-(2,2-dichloro-1,1-difluoroethoxy)phenyl)amino)carbonyl)-2-chlorobenzamide.

M.P. 162°-164° C.

Analysis: Calcd: C, 39.01; H, 1.84; N, 5.69. Found: C, 39.64; H, 1.89; N, 5.69.

N-(((2,5-Dichloro-4-(2-bromo-1,1,2-trifluoroethoxy)-phenyl)amino)carbonyl)-2-chlorobenzamide.

M.P. 129°-132° C.

Analysis: Calcd: C, 36.92; H, 1.74; N, 5.38. Found: C, 37.76; H, 1.78; N, 5.55.

In addition to the above described preparative methods, many of the compounds of this invention can be made by reacting a compound having the formula

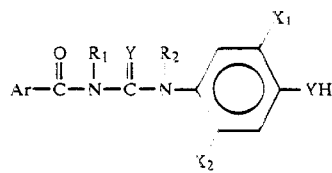

wherein all of the substituents are as above-defined, with a haloalkene as is known in the art.

The compounds of the present invention are normally crystalline solids of low solubility in water and of moderate solubility in many organic solvents. The compounds have low phytotoxicity and have exceptional activity in the control of various undesirable agricultural, household and veterinary insect pests.

Representative of the various insects which can be controlled by the active compounds of the present invention are members of the orders Lepidoptera, Coleoptera, Diptera, Orthoptera, Homoptera, Thysanoptera and Acarina. They are active against normally sensitive and resistant species at some stages of development. Examples of insect pests comprising the above include the tobacco budworm (*Heliothis virescens*), the beet armyworm (*Spodoptera exigua*), the Egyptian cotton leafworm (*Spodoptera littoralis*), the American bollworm (*Heliothis armigera*), the diamond-back moth (*Plutella maculipennis*), the gypsy moth (*Lymantria dispar*), the cutworm (*Agrotis segetum*), the Mediterranean flour moth (*Ephestia kuehniella*), the Colorado potato beetle (*Leptinotarsa decimlineata*), the mustard beetle (*Phaedon cochleariae*), the cotton boll weevil (*Anthonomus grandis*), the Mexican bean beetle (*Epilachna varivestis*), the khapra beetle (*Trogoderma granarium*), the housefly (*Musca domestica*), the lesser housefly (*Fannia canicularis*), the Mediterranean fruit fly (*Ceratitis capitata*), the black blow fly (*Phormia regina*), the cabbage rootfly (*Hylemya brassicae*), the yellow fever mosquito (*Aedes aegypti*), the malaria mosquito (*Anopheles stephensi*), the desert locust (*Schistocerca gregaria*), the migratory locust (*Locusta migratoria*), the German cockroach (*Blattells germanica*), the American cockroach (*Periplaneta americana*), the pear psylla (*Psylla pyricola*), the onion thrips (*Thrips tabaci*), and the citrus rust mite (*Phyllocoptruta oleivora*).

The compounds are highly active and can be employed to kill insects outright and/or to prevent adult emergence from juvenile forms of the insect. In such applications, the insect to be controlled and/or its habitat is contacted or treated with an insecticidal amount of one or more of the compounds of the present invention. The compounds may be administered orally to warm blooded animals from which they are excreted unchanged and they effectively combat the larvae of certain feces inhabiting insects, e.g., the face fly, horn fly and buffalo fly.

For all such uses, these compounds can be employed in unmodified form. However, the present invention embraces the use of an insecticidally-effective amount of the active ingredients in composition form with a material known in the art as an adjuvant or carrier.

Thus, for example, compositions employing one or a combination of these active ingredients can be in the form of a liquid or a dust; and the adjuvant employed can be any one of a plurality of materials including aromatic solvents, petroleum distillates, water or other liquid carriers, propellant substances, surface-active dispersing agents, light absorbers and finely-divided carrier solids.

The exact concentration of one or a combination of the compounds of the present invention in a composition thereof with an adjuvant therefor can vary; it is only necessary that one or a combination of the compounds be present in a sufficient amount so as to make possible the application of an insecticidally-effective or inactivating dosage.

Generally, for practical applications, one or a combination of these active ingredients can be broadly applied to the insect larvae or their habitat in compositions containing from about 0.0001 to about 98 percent by weight of the compounds.

The invention is further illustrated by the following examples. In the beet armyworm test, cotton leaves were dipped in aqueous suspensions of the chemicals, dried, excised and placed into petri dishes with five second-instar beet armyworm (*Spodoptera exigua*) larvae. Mortality counts were made five days later. The tobacco budworm test was the same except that five tobacco budworm (*Heliothis virescens*) larvae were placed onto the treated leaves. The results are summarized below:

Compound A

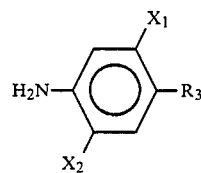

| Compound A | Percent Morality at Indicated Dosage | | | | | |
|---|---|---|---|---|---|---|
|  | 10 | 6.25 | 5 | 2.5 | 1.25 | 0.62 |
| Beet Armyworm | 100 | 100 | 93 | 87 | 60 | 0 |
| Tobacco Budworm | 100 | 93 | 80 | 53 | 0 | 0 |
| Cabbage Looper | 100 | NT | 100 | 100 | 60 | 40 |

In further embodiments, the compounds of the present invention or compositions containing the same, can be advantageously employed in combination with one or more additional pesticidal compounds. Such additional pesticidal compounds may be insecticides, nematocides, acaricides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

We claim:
1. A compound having the formula

$$H_2N-\underset{X_2}{\overset{X_1}{\bigcirc}}-R_3$$

wherein $X_1$ and $X_2$ are independently halogen and $R_3$ is a $C_1-C_4$ haloalkoxy or haloalkylthio group.

2. 2,5-Dichloro-4-(1,1,2,2-tetrafluoroethoxy)-benzenamine.

3. 2,5,-Dichloro-4-(2-chloro 1,1,2-trifluoroethoxy) benzenamine.

* * * * *